United States Patent
Weston

(10) Patent No.: US 9,072,878 B2
(45) Date of Patent: Jul. 7, 2015

(54) TATTOO NEEDLE AND METHOD FOR MAKING AND USING SAME

(76) Inventor: Mark A. Weston, Cape Haze, FL (US)

(*) Notice: Subject to any disclaimer, the term of this patent is extended or adjusted under 35 U.S.C. 154(b) by 161 days.

(21) Appl. No.: 13/196,590

(22) Filed: Aug. 2, 2011

(65) Prior Publication Data

US 2012/0029549 A1    Feb. 2, 2012

Related U.S. Application Data

(60) Provisional application No. 61/369,786, filed on Aug. 2, 2010.

(51) Int. Cl.
*A61B 17/34* (2006.01)
*A61M 37/00* (2006.01)

(52) U.S. Cl.
CPC ....... *A61M 37/0076* (2013.01); *Y10T 29/49826* (2015.01)

(58) Field of Classification Search
CPC .............. A61M 37/0076; A61M 37/0084
USPC ........... 606/167, 181, 185–187; 604/164.01, 604/173, 272, 22, 46, 117, 118, 289, 506; 81/9.22; 128/898
See application file for complete search history.

(56) References Cited

U.S. PATENT DOCUMENTS

2005/0066775 A1*  3/2005  Chen ............................. 81/9.22
2011/0042847 A1*  2/2011  Ogawa et al. ................ 264/219

FOREIGN PATENT DOCUMENTS

CN   201862140 U    *   6/2011
DE   29701929        *   4/1997
JP   2000342332 A   *  12/2000   ............. A45D 44/00

OTHER PUBLICATIONS

Machine Translation performed Oct. 12, 2012 for JP 2003-42332.*
Machine Translation performed Oct. 15, 2012 for abstract of DE 29701929.*
"SEIRIN Needles." SEIRIN Acupuncture Needles. www.ihasamos.com. Aug. 22, 2009.*
"Round." PainfulPleasures. www.painfulpleasures.com. Mar. 4, 2006.*
"Advance Shader Half Star & Star." Advance Shader Star. www.tattoonet.asia. May 24, 2008.*
"Scalp Tattoos Cure Baldness." www.flashnews.com. Mat, 10, 2010.*
English machine translation of CN 201862140 U.*

* cited by examiner

*Primary Examiner* — Katherine M Shi
(74) *Attorney, Agent, or Firm* — Gifford, Krass, Sprinkle, Anderson & Citkowski, P.C.

(57) ABSTRACT

A tattoo needle apparatus that may be used in connection with replicating hair follicles on a scalp of a client is disclosed along with a method of constructing the needle. The needle may include a shank and a needle head secured to the shank. The needle head may include a bundle of three pins (needles), with a point (tip or apex) of each pin being bent, deformed, deflected or otherwise curved inwardly toward a longitudinal axis of the bundle of pins. The method for constructing the needling may include securing the pins in a bundle, curving the points, and mounting the bundle to a needle shank.

6 Claims, 3 Drawing Sheets

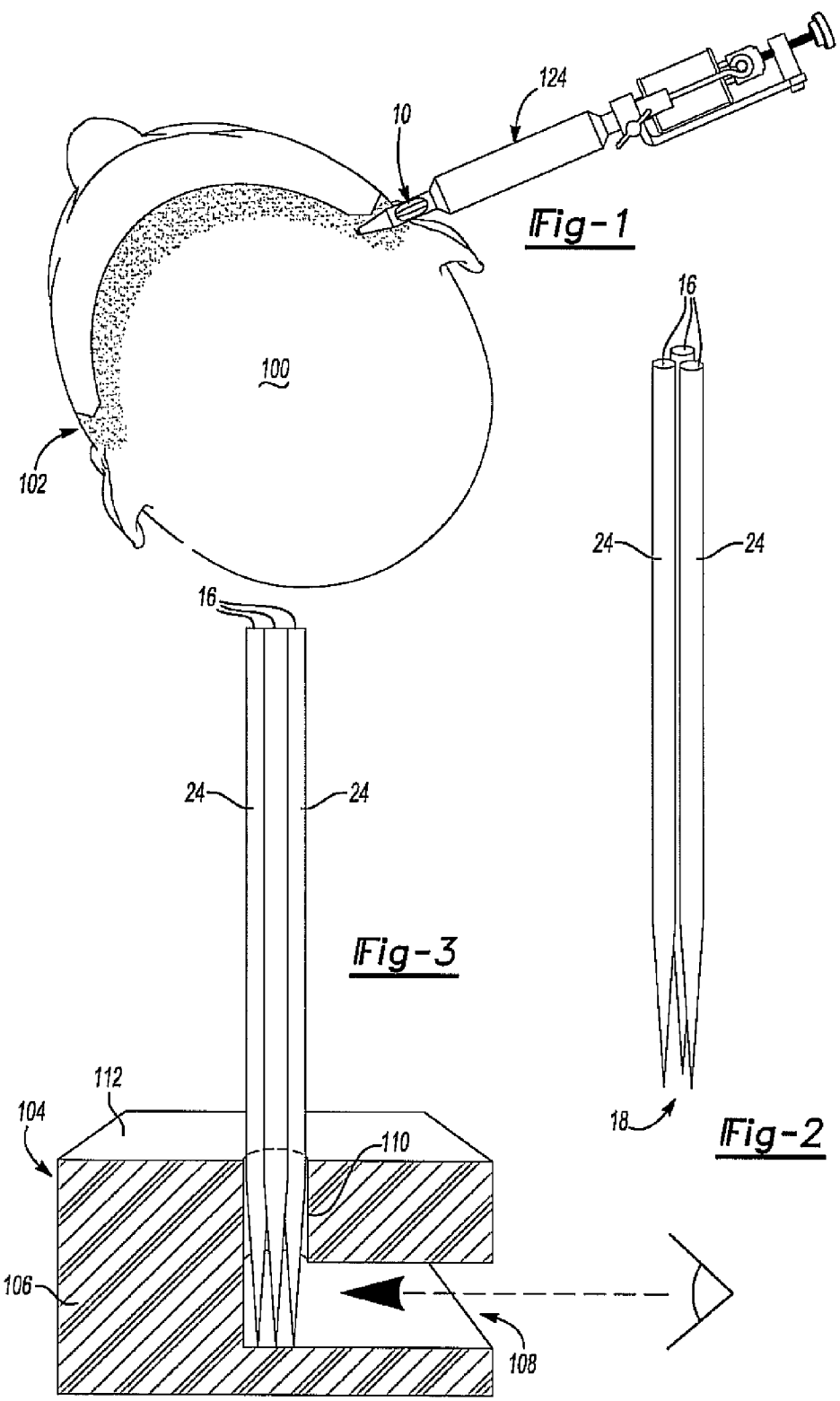

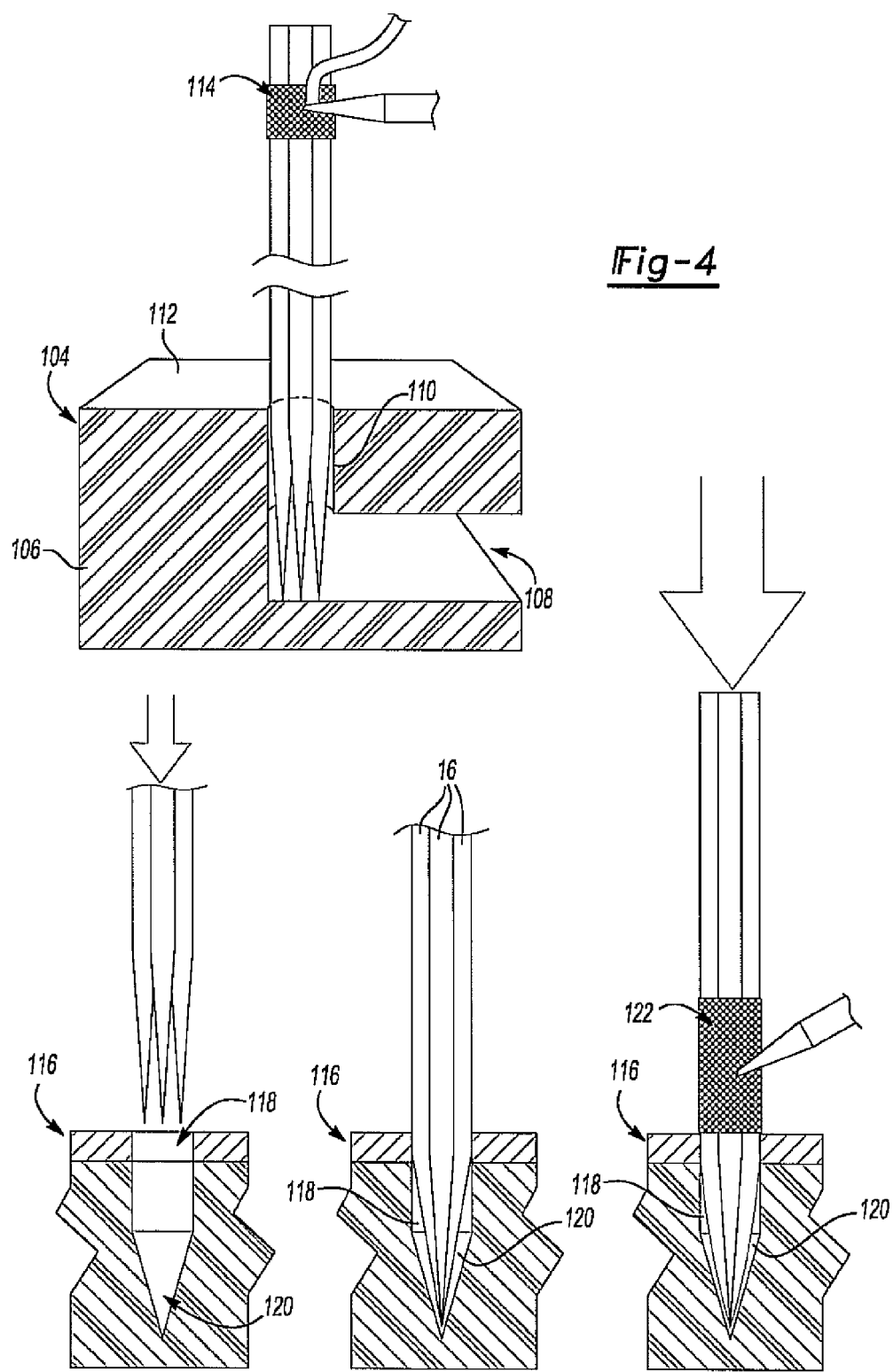

TATTOO NEEDLE AND METHOD FOR MAKING AND USING SAME

CROSS-REFERENCE TO RELATED APPLICATIONS

This application claims priority from U.S. Provisional Patent Application No. 61/369,786, filed Aug. 2, 2010, the entire disclosure of which is incorporated herein by reference.

FIELD OF THE INVENTION

A needle apparatus is disclosed for tattooing the skin of the scalp with improved characteristics, along with a method for making and using the needle.

BACKGROUND OF THE INVENTION

Tattoos to replicate lost hair follicles (particularly on the scalp) are not well known, but are becoming more popular. But a problem exists when available tattoo needles are used to try and replicate a hair follicle.

A typical tattoo needle may include a set of three separate pins bundled together to form the needle. The pins used in available tattoo needles have diameters that are far too large to effectively recreate the look of a hair follicle. As a result, the "follicles" created by available tattoo needles are much larger than the real thing—leaving the wearer of the tattoo with a poor replication of a non-bald head.

Smaller single pin tattoo needles are available. However, a single pin needle would not function well, if at all, since (unlike a three pin needle) it may not draw in or retain ink, or the ink may be rubbed off the needle as the needle pierces the skin. Moreover, even if a single pin needle could be made to function properly it would take an incredible amount of time to duplicate hair follicles using those needles and it is also difficult to create a pattern of spacing for the follicles.

The larger diameter of conventional tattoo needles do not create the size closest to a hair follicle and smaller needles make it difficult to create a realistic pattern of simulated hair follicles. Thus, prior art needles are unsatisfactory and the need for improvement exists.

SUMMARY OF THE INVENTION

A tattoo needle apparatus is disclosed that may be used in connection with replicating hair follicles on a scalp of a client. The needle may include a shank and a needle head secured to the shank. The needle head may include a bundle of three pins (needles), with a point (tip or apex) of each pin being bent, deformed, deflected or otherwise curved inwardly toward a longitudinal axis of the bundle of pins. Also disclosed is a method for constructing the needle that includes securing the pins in a bundle, curving the points, and mounting the bundle to a needle shank.

BRIEF DESCRIPTION OF THE DRAWINGS

FIG. 1 is a planar view showing tattoos applied to a client's scalp to replicate a non-bald scalp using an embodiment of the disclosed tattoo needle;

FIG. 2 is a perspective side view of a bundle of needle pins;

FIG. 3 is a perspective side view of the bundle of needle pins of FIG. 2 positioned in a jig to retain the pins in a bundled configuration to align the points of the pins;

FIG. 4 is a perspective side view of the bundle of needle pins of FIG. 2 positioned in a jig and showing the shafts of the pins soldered together;

FIG. 5A is a planar side and partial cutaway view of the bundle of needle pins of FIG. 4 positioned proximate a second jig operable to configure the points of the pins;

FIG. 5B is a planar side and partial cutaway view of the bundle of needle pins of FIG. 4 inserted in the second jig;

FIG. 5C is a planar side and partial cutaway view of the bundle of FIG. 4 inserted in the second jig and downward pressure being applied to the bundle to inwardly curve the point of each pin;

DETAILED DESCRIPTION OF THE PREFERRED EMBODIMENT

Figure 6:
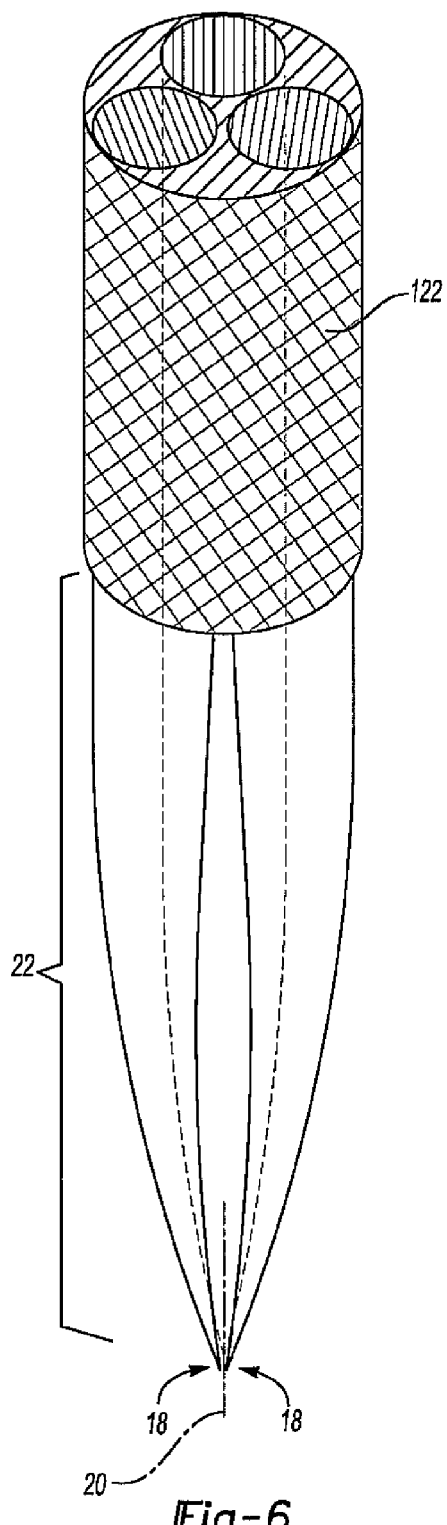
FIG. 6 is a perspective side view of the bundle/tattoo needle head following the operation shown in FIG. 5C.

A tattoo needle for use in connection with the replication of hair on a client's scalp may have a needle head and a shank (or arm). The needle head may include a bundle of three pins (needles), with the point of each pin being bent, deflected, deformed or otherwise curved inwardly toward a longitudinal axis of the bundle. The curved points or ends of the pins of the needle head may thus create a working tip or end for the tattoo needle having a diameter that at least a portion of which may be less than the diameter of a shaft of one of the pins. Additionally, while the disclosed needle has been discussed as being used on a person's scalp, it will be appreciated that it may also be used for eyeliner, recreating eyebrows, and facial hair such as a beard or mustache.

Referring now to FIGS. 1, 2, 6 and 7, a tattoo needle 10 that may be used in connection with replicating hair follicles on a scalp 100 of a client 102 may include a shank (or arm) 12 and a needle head 14 that is secured to the shank 12. The needle head 14 may include a bundle of three pins 16 (needles), with a point (tip) 18 of each pin 14 being bent, deformed, deflected or otherwise curved inwardly toward a longitudinal axis 20 of the bundle of pins 16. The curved points 18 of the pins 16 of the head 14 of the tattoo needle 10 may thus create a working tip 22 or end for the needle 10 having a diameter at least a portion of which may be less than the diameter of a shaft 24 of one of the pins 16.

Referring now to FIG. 2, the pins 16 of the head 14 of the needle 10 may all be of the same size, type and construction. In one embodiment each pin may be a 0.22 mm tapered tattooing needle. For example, each pin 16 may be a stainless steel #6 BugPin sharp long tapered needle sold by Cam Tattoo Supply, which have a (shaft) diameter of 0.0083 (0.22 mm). It will, however, be appreciated that other pins 16 may also be used to construct the needle head 14, such that those having a diameter between 0.18 mm and 0.22 mm. It will further be appreciated that the head 14 may be constructed using pins 16 having a diameter between 0.04 mm (acupuncture needles (0.04 mm-0.06 mm)) and 0.28 mm.

Referring now to FIGS. 2-4, the pins 16 may be arranged in a "triangular"-type bundle such that at least a portion of the shaft 24 of each pin 16 may contact at least a portion of the shaft 24 of the other two pins 16. Then, as best shown in FIG. 3, the pins 16 the bundle may be positioned in a first or grouping jig 104 to align the points 18.

Still referring to FIGS. 2-4, and as best shown in the embodiment of FIG. 3, the grouping jig 104 may include a base 106 having a channel 108 and an aperture 110 that extends through the base 106 from an exterior face 112 to the channel 108. The bundle of pins 16 may be placed in the aperture 110 (which may be dimensioned to tightly retain the pins 16 in their bundled arrangement) such that the points 18 of the pins 16 rest on a planar floor 112 of the channel 108 (which may run perpendicular to the longitudinal axis of the pins 16). The horizontal alignment of the pins 16 (i.e., that all three pins 16 are resting on the floor 112 of the channel 108) may be confirmed by visual examination of the pins 16 through the channel 108.

As best shown in FIG. 4, once properly positioned in the grouping jig 104, the shafts 24 of the pins 16 may then be secured together by soldering 114 or like means known in the art.

Referring now to FIGS. 5A-5C, 6 and 8, the points 18 of the soldered bundle of pins 16 of the head 14 may be bent, deflected, deformed or otherwise curved inwardly using a second or tightening jig 116. The tightening jig 116 may include a recess 118 having a conical portion 120. Alternatively, the jig 116 may simply include a conical shaped recess.

As shown in FIGS. 5A, 5B and 6, the soldered bundle of pins 16 may be positioned "pointwise" in the recess of the jig 116. Then, once in position, downward force may be applied to the bundle such that the points 18 of the pins 16 deform inwardly toward the longitudinal axis 20 of the bundle. Additionally, or alternatively, the force applied may be sufficient to cause the shaft 24 of each pin 16 to flex or "bow" outwardly and thereby cause the points 18 of the pins 16 to deflect inwardly in the recess 118. In either case, and as best shown in FIG. 5C, the shafts 24 of the pins 16 of the bundle are further soldered 122 to retain the pins 16 in position. In one embodiment the bundle is soldered between 2.0 and 2.3 mm (and in one embodiment about 2.17 mm) up from the apex of the points 18 of the pins 16. The soldering may also terminate at a position along the shaft 24 of each pins 16 such that the widest useable point (i.e., an area of the pin below the solder that may penetrate a client's skin during use) of the working end or tip 22 of the needle head 14 has a diameter (around the bundle) of about 0.36 mm or less (down to about 0.20 mm), and preferably no more than about 0.40 mm. And, it being further appreciated that when the "bowing" method of deflecting the pins 16 is used, the pins 16 may be simultaneously bowed and soldered so that the points 18 are fixed in an inwardly deflected orientation.

As mentioned supra, the needle head 14 may be constructed using pins 16 having a diameter between 0.04 mm (acupuncture needles (0.04 mm-0.06 mm)) and 0.28 mm. It will also be appreciated, however, that the terminal end of each point may have a diameter of about 0.12, so that the diameter across the terminal ends of curved points of the needle head 14 may be about 0.05 mm to 0.10 mm.

Figure 7:
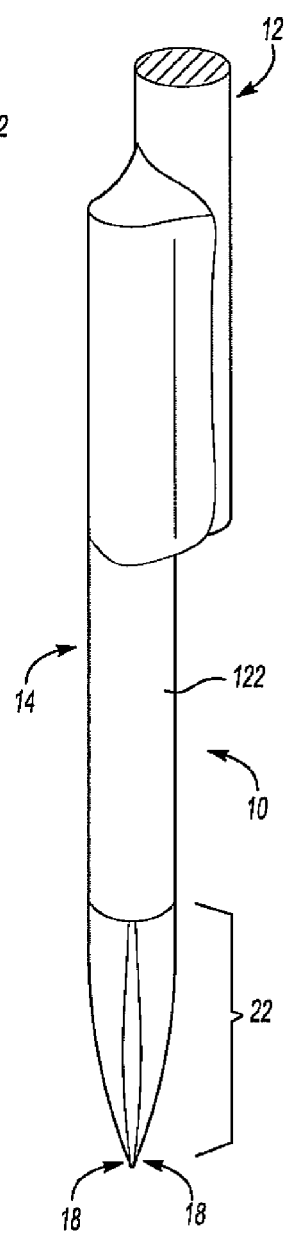
FIG. 7 is a perspective side view of the bundle/tattoo needle head of FIG. 6 secured to an arm or shank for mounting the bundle/tattoo needle to a tattoo machine.
Figure 8:
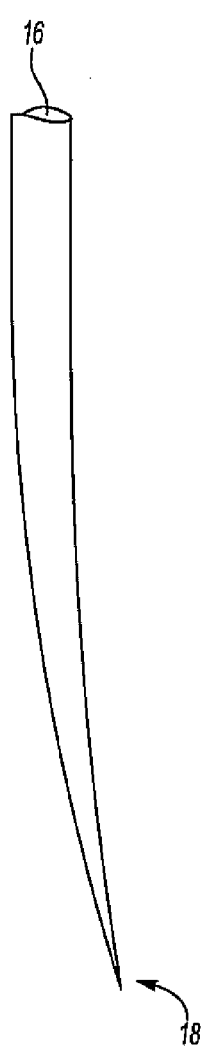
FIG. 8 is a perspective side view of a pin of the bundle/tattoo needle head shown in FIG. 6.

Referring now to FIGS. 1 and 7, the needle head 14 may be secured to the shank (or arm) 12 by soldering or like means known in the art. It will be appreciated that the shank 12 may be configured so that the needle 10 may be used on any commercially available tattoo machine 124, including cosmetic machines sold under the name Bella Co., Ltd., BioTouch, Amiea and Nouveau, and standard machines like those sold under the name Cam Supply, Kingpin Tattoo Supply, Technical Tattoo Supply, Spaulding-Rogers, Superior Tattoo Equipment, Eikon Device, Inc., National Tattoo Supply, and Unimax Supply Co., Inc.

Having described certain embodiments of my method and apparatus, various other embodiments may become apparent to those of skill in the art that do not depart from the scope of the claims set forth below.

I claim:

1. A method comprising:
   providing a tattoo needle having an arm and a needle head secured to the arm, the needle head including three pins, each pin having a point and a shaft and the pins being secured together in a bundle so that the shaft of each pin contacts at least a portion of the shaft of two pins, each pin also having a predetermined shaft diameter;
   providing a jig including a recess having a conical shaped portion;
   inserting the bundle into the recess so that each pin is tapered inward toward a longitudinal axis of the bundle by the conical shaped portion and so that the points of all the pins collectively form a needle head;
   providing a tattoo machine;
   positioning the tattoo needling on the tattoo machine;
   applying the tattoo needle to the scalp of a human using the tattoo machine to create the appearance of a hair follicle on the scalp.

2. The method of claim 1, wherein the step of providing a tattoo needle having an arm and a needle head secured to the arm, the needle head including three pins, further comprises including pins have a diameter of 0.00075 inches and a length of 1.27 inches.

3. The method of claim 1, wherein the step of applying the tattoo needle to the scalp of a human using the tattoo machine to create the appearance of a hair follicle on the scalp further comprises, using the tattoo needle to place a plurality of micro points of an ink randomly on either side of a predetermined hairline of a human.

4. The method of claim 1, wherein the step of applying the tattoo needle to the scalp of a human using the tattoo machine to create the appearance of a hair follicle on the scalp further comprises, using the tattoo needle to place a plurality of micro points of an ink randomly on either side of a predetermined hairline of a human, and from the predetermined hairline back ¾ of an inch, and down the temple area of the human.

5. The method of claim 1, further comprising examining the tattoo needle for at least one of hooking or blunting following the step of applying the tattoo needle to the scalp of a human.

6. The method of claim 5, further comprising replacing the tattoo needle with a second tattoo needle following the step of examining the tattoo needle.

* * * * *